(12) United States Patent
Orrego et al.

(10) Patent No.: US 7,718,191 B2
(45) Date of Patent: May 18, 2010

(54) PHARMACEUTICAL PRODUCT WHICH IS USED TO REDUCED OR STOP MODERATE OR SEVERE SNORING

(75) Inventors: Augusto Larrain Orrego, Avendia Kennedy 7085, Las Condes, Santiago (CL); Francesca Morri, Santiago (CL)

(73) Assignee: Augusto Larrain Orrego (CL)

( * ) Notice: Subject to any disclaimer, the term of this patent is extended or adjusted under 35 U.S.C. 154(b) by 1072 days.

(21) Appl. No.: 10/536,549

(22) PCT Filed: Dec. 1, 2003

(86) PCT No.: PCT/IB03/05652

§ 371 (c)(1),
(2), (4) Date: Apr. 11, 2006

(87) PCT Pub. No.: WO2004/050070

PCT Pub. Date: Jun. 17, 2004

(65) Prior Publication Data

US 2006/0233872 A1    Oct. 19, 2006

(30) Foreign Application Priority Data

Dec. 2, 2002   (CL) .................................. 2760/2002

(51) Int. Cl.
   *A61K 9/48* (2006.01)
(52) U.S. Cl. ...................................................... 424/451
(58) Field of Classification Search .................... None
   See application file for complete search history.

(56) References Cited

U.S. PATENT DOCUMENTS 6,114,346 A   9/2000   Harris et al. ................ 514/290

OTHER PUBLICATIONS

Larrain et al, "Treatment of severe snoring with a combination of pseudoephedrine sulfate and domperidone", J. Clin. Sleep Med., 2006;2(1)21-25.*
Fireman P: "Therapeutic Approaches to Allergic Rhinitis: Treating the Child" Journal of Allergy and Clinical Immunology, Mosby-Yearly Book, Inc, US, vol. 105, No. 6, 2000, pp. S616-S621, Xpoo1097923, ISSN: 0091-6749, Abstract, Table V.

* cited by examiner

*Primary Examiner*—Humera N Sheikh
*Assistant Examiner*—Bethany Barham
(74) *Attorney, Agent, or Firm*—Jack Schwartz and Associates, PLLC

(57) ABSTRACT

The invention relates to the novel use of a pharmaceutical product which combines domperidone and pseudoephedrine sulphate substances and which can be used to reduce or stop moderate or severe snoring.

6 Claims, No Drawings

PHARMACEUTICAL PRODUCT WHICH IS USED TO REDUCED OR STOP MODERATE OR SEVERE SNORING

BACKGROUND

The present invention is applied in the field of medicine, more specifically to treat snoring.

Interest in sleep apnea has increased in recent years due to studies that have been carried out that show that it is a very common condition, which, if left untreated, can be linked to serious cardiovascular illnesses. Access to more trustworthy diagnostic methods and effective treatment help to advance the research and evaluation of diagnosis and therapy by different specialists.

At the moment there are a number of homeopathic remedies which use natural plants and herbs that fluidify the mucous secretions of the palate, to aid the flow of air. Also, there are several 'sprays', nasal drops and local or general aromatherapy, nasal lubricants and external correctors to dilate the nostrils. In the United States, more than 50 devices have been patented, to be used locally such as sosmnoguard amongst others and there are special inflatable pillows to prevent people sleeping on their back, ribbons or collars that close the mouth by raising the jaw.

(Stamped)

An Internet search detected 158,080 sites that provide information about treatment for snorers, in which you can see a whole range of treatments from hypnosis to surgery.

There are various invasive treatments, but the most common are the following:

1. Snoreplasty by injection that infiltrates alcohol or sodium tetradecyl sulphate in the palate to harden it. Its effects take weeks to appear and according to its authors, the resulting sclerosis is beneficial.

2. Uvulopalatoplasty by laser, which is very fashionable at the moment, even in our country. Said technique involves the surgical ablation by laser of the soft palate and the uvula to create a wider airway. Apart from its aggressiveness, its results are questionable as reported in a separate study by ENT specialists (Arch. Otolaryngol. Head Neck Surg., 2001, 127, 412-417); that shows a 43% initial satisfaction rate with the procedure which decreases in later check ups. In said publication, the authors note that it can produce fibrosis and adherence of the residual palate, further decreasing the airway making the sleep apnea appear in a large number of patients that previously did not have it.

The latest study published was aimed at nighttime nasal congestion that would be an important independent factor in the habitual snoring without true apnea.

The authors carried out polysomnography on 4,916 patients in Wisconsin (United States), and concluded that the patients with chronic severe nasal congestion were more likely to be habitual snorers (Arch. Intern, Med., 2001, 161, 1514-1519.

Finally, the use of CPAP ought to be mentioned which is a pressurised oxygen infuser system machine for patients with sleep apnea and who need to use it all through the night. Its commercial value is 1,000,000 Chilean pesos for each case and our Health System is not able to provide it as happens in other countries.

The use of efficient surgery in cases of gastroesophageal reflux, by this author at the beginning of the 1970s, led to multiple consequences that were not related before. The patients reported that the day after the operation they could breathe better, asthmatics stopped having attacks and the obstructive bronchitis disappeared in many unweaned babies. This motivated the author to carry out a 15 year study, which was the first study carried out with rigorous testing and method and which has been internationally recognised. During 1974, a relationship between an alteration in the larynx and the gastroesophageal reflux became apparent, which is now known as "acid laryngitis". This alteration causes congestion of the respiratory mucous, where the main symptom is the presence of "hoarseness". Also, it is important to note that in the majority of cases, this lesion does not have symptoms of oesophageal reflux or they are very mild. Its incidence in the normal population is high. It was the concomitance of the disappearance of snoring in the operated cases, reported by family members, which motivated the author to look for a medical treatment to alter the respiratory pathway that exists in snorers that do not have an obvious obstructive anatomical alteration (adenoids, noticeable deviation of nasal septum, etc). The association of the larynx lesion with congestion, steered towards the possibility of using a decongestant along with a substance that increases the gastric and oesophageal motility, which protects acid reflux. Nevertheless, substances that reduce or eliminate the acid secretion cannot be added, because they obstruct the absorption of the aforementioned drug and also the vast majority of patients do not report problems from the presence of gastric reflux content.

This is how PVA103 came about, which is comprised of pseudoephedrine sulphate (60 mg) and domperidone (10 mg) per capsule. Both drugs have been extensively studied (pseudoephedrine appears on 71,000 internet sites and domperidone appears on 9,080 internet sites). In Chile, pseudoephedrine was included in drugs that do not need medical prescription from 1 May 2000. The Director of the Institute of Public Health (ISP) Sr. Gonzalo Navarrete, said at the time "it does not make sense to restrict it, because it is not a dangerous substance". Also, the current Director of the ISP Sra. Jeannette Vega, stated on 17 Aug. 2002 that "drugs that do not require medical prescription do not carry the risk of improper use, abuse or addiction", the side effects that occasionally appear are not severe and are reversible after stopping the medication, these medicines are safe and effective for the population to consume."

As a mid-range, there is the option of using a combination of pseudoephedrine sulphate (60 mg) and pseudoephedrine hydrochloride (120 mg).

The combination of the pseudoephedrine substances with domperidone is new and has not been presented in any country in the world and especially not for its use in snorers. 25% of the population can be classed as severe or moderate habitual snorers. It is a disturbance that can cause problems for co-inhabitants and the possibility of eliminating this problem with a simple medication is very important.

In Chile pseudoephedrine forms part of several preparations, it has been combined with ascorbic acid in 4 preparations, with bromophenylamine in 1 preparation, with caffeine in 2 preparations, with cetirizine in 2 preparations, with chlorphenamine in 45 preparations, with codeine in 15 preparations, with eucalyptus in 1 preparation, with loratadine in 10 preparations, with noscapine in 3 preparations, with paracetamol in 31 preparations, with propyphenazon in 1 preparation, with retinal in 1 preparation, with tolu in 1 preparation and with triprolidine in 2 preparations.

The PVA103 preparation has been administered to volunteers in the form of a capsule 30 minutes after the evening meal in which a moderate consumption of alcohol is permitted or two glasses of wine. If after 4 hours the volunteer starts to snore again, he/she can take another dose. In the trials no problems were noted and the result, the disappearance of snoring, is notable.

Apart from the obvious benefits for the patient this preparation is low cost with the consequent large-scale use and benefit, it constitutes a new use of two known compounds, which if administered in the dose indicated above, constitutes a new compound that resolves the technical problem that does not have equivalent solution.

The invention claimed is:

1. A composition comprising a combination of pseudoephedrine sulphate and domperidone wherein the composition is used to alleviate or eliminate snoring in a moderate or severe non-pathological snorer.

2. The composition comprising a combination of pseudoephedrine sulphate and domperidone according to claim 1, wherein said composition is provided as an orally administered capsule.

3. The composition comprising a combination of pseudoephedrine sulphate and domperidone according to claim 1, wherein said combination includes an average dose of 60 mg of pseudoephedrine and 10 mg of domperidone.

4. The composition comprising a combination of pseudoephedrine sulphate and domperidone according to claim 1, wherein the composition is provided as a daily capsule for consumption 30 minutes after an evening meal.

5. The composition comprising a combination of pseudoephedrine sulphate and domperidone according to claim 1, wherein said combination includes a dose of 60 mg pseudoephedrine sulphate and 120 mg of pseudoephedrine hydrochloride.

6. The composition comprising combination of pseudoephedrine sulphate and domperidone according to claim 4, wherein said composition may be re-administered at least 4 hours after ingesting the capsule if snoring starts again.

* * * * *